US 6,555,723 B2

(12) United States Patent
Schiffino

(10) Patent No.: US 6,555,723 B2
(45) Date of Patent: *Apr. 29, 2003

(54) CONTINUOUS MANUFACTURING PROCESS FOR ALPHA-OLEFINS

(75) Inventor: Rinaldo S. Schiffino, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/921,818

(22) Filed: Aug. 3, 2001

(65) Prior Publication Data

US 2002/0019575 A1 Feb. 14, 2002

Related U.S. Application Data

(63) Continuation-in-part of application No. 09/906,974, filed on Jul. 17, 2001.
(60) Provisional application No. 60/218,888, filed on Jul. 18, 2000, and provisional application No. 60/222,786, filed on Aug. 3, 2000.

(51) Int. Cl.[7] ............................. G07C 2/08; G07C 2/14
(52) U.S. Cl. ..................... 585/521; 585/511; 585/512; 585/513; 585/522; 585/527
(58) Field of Search ............................. 585/511, 512, 585/513, 521, 522, 527

(56) References Cited

U.S. PATENT DOCUMENTS

| 4,020,121 A | 4/1977 | Kister et al. |
| 5,955,555 A | 9/1999 | Bennett |
| 6,103,946 A | 8/2000 | Brookhart, III et al. |

OTHER PUBLICATIONS

I. Kroschwitz, et al., Ed., Kirk–Othmer Encyclopedia of Chemical Technology, 4th Ed., vol. 17, John Wiley & Sons, New York, p. 839–858.

*Primary Examiner*—Thuan D. Dang

(57) ABSTRACT

A manufacturing process for α-olefins using certain iron containing ethylene oligomerization catalysts together with alkylaluminum cocatalysts, in which using a low ratio of Al:Fe in the process results in a lowered formation of undesired polyethylene waxes and polymer. This results in less fouling of the process lines and vessels in the manufacturing plant.

12 Claims, No Drawings

CONTINUOUS MANUFACTURING PROCESS FOR ALPHA-OLEFINS

CROSS-REFERENCE TO RELATED APPLICATION

This application is a continuation-in-part of copending application Ser. No. 09/906,974 (filed Jul. 17, 2001), entitled "MANUFACTURING PROCESS FOR ALPHA-OLEFINS", which claims priority under 35 U.S.C. §119 from U.S. Prov. Appl. Ser. No. 60/218,888 (filed Jul. 18, 2000), which is incorporated by reference herein for all purposes as if fully set forth. This application further claims priority under 35 U.S.C. §119 from U.S. Prov. Appl. Ser. No. 60/222,786 (filed Aug. 3, 2000), which is also incorporated by reference herein for all purposes as if fully set forth.

FIELD OF THE INVENTION

A continuous manufacturing process for α-olefins using certain iron containing ethylene oligomerization catalysts together with alkylaluminum cocatalysts, in which using a low ratio of Al:Fe in the process results in a lowered formation of undesired polyethylene waxes and polymer.

TECHNICAL BACKGROUND

α-Olefins are important items of commerce, billions of kilograms being manufactured yearly. They are useful as monomers for (co)polymerizations and as chemical intermediates for the manufacture of many other materials, for example detergents and surfactants. Presently most α-olefins are made by the catalyzed oligomerization of ethylene by various catalysts, especially certain nickel complexes or aluminum alkyls, see for instance U.S. Pat. No. 4,020,121 and I. Kroschwitz, et al., Ed., *Kirk-Othmer Encyclopedia of Chemical Technology*, 4$^{th}$ Ed., Vol. 17, John Wiley & Sons, New York, p. 839–858.

Recently, as reported in U.S. Pat. No. 5,955,555 and U.S. Pat. No. 6,103,946, both of which are hereby incorporated by reference herein for all purposes as if fully set forth, it has been found that iron complexes of certain tridentate ligands are excellent catalysts for the production of α-olefins from ethylene. Among the options for using such catalysts are those in which the iron complexes are used in conjunction with a cocatalyst, particularly an alkylaluminum cocatalyst such as an alkylaluminoxane.

It has recently been found, particularly in continuous processes using such iron complexes, that high molar ratios of Al:Fe lead to the undesirable formation of polyethylene waxes and polymers, which tend to foul the oligomerization apparatus. It has now been found that lower Al:Fe ratios diminish the formation of these undesirable polyethylenes, while not otherwise significantly deleteriously affecting the process.

SUMMARY OF THE INVENTION

This invention concerns a continous process for the production of a linear α-olefin product, comprising the step of contacting, in a continuous reactor, process ingredients comprising an ethylene oligomerization catalyst composition, ethylene and a cocatalyst, wherein:

(a) the ethylene oligomerization catalyst composition comprises an iron complex of a compound of the formula

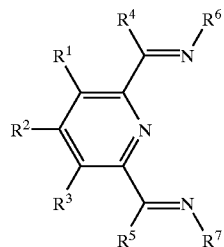

(I)

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom;

(b) the cocatalyst comprises an alkyl aluminum compound; and (c) the molar ratio of Al in the cocatalyst to Fe in the ethylene oligomerization catalyst is about 2000 or less.

This invention further concerns an improved continous process for the production of a linear α-olefin product, the process comprising the step of contacting, in a continuous reactor, process ingredients comprising an ethylene oligomerization catalyst composition, ethylene and a cocatalyst, wherein:

(a) the ethylene oligomerization catalyst composition comprises an iron complex of a compound of the formula

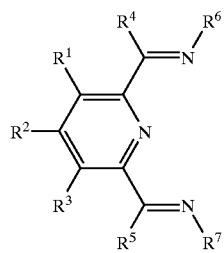 (I)

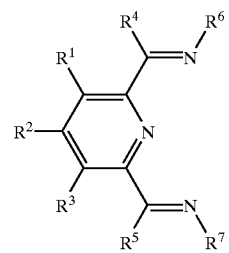 (I)

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom; and (b) the cocatalyst comprises an alkyl aluminum compound;

wherein the improvement comprises reducing the formation of polyethylene waxes and polymers in the linear α-olefin product by contacting the process ingredients at a molar ratio of Al in the cocatalyst to Fe in the ethylene oligomerization catalyst of less than about 2000.

This invention also concerns a method for reducing the formation of polyethylene waxes and polymers in a continuous process for the production of a linear α-olefin product, said continuous process comprising the step of contacting, in a continuous reactor, process ingredients comprising an ethylene oligomerization catalyst composition, ethylene and a cocatalyst, wherein:

(a) the ethylene oligomerization catalyst composition comprises an iron complex of a compound of the formula wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom; and (b) the cocatalyst comprises an alkyl aluminum compound;

said method for reducing comprising the step of contacting said process ingredients in amounts such that the molar ratio of Al in the cocatalyst to Fe in the ethylene oligomerization catalyst is about 2000 or less.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION OF THE PREFERRED EMBODIMENTS

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the oligomerization process or operation of the oligomerization catalyst system. If not otherwise stated, it is preferred that substituted hydrocarbyl groups herein contain 1 to about 30 carbon atoms. Included in the meaning of "substituted" are rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include halo (fluoro, chloro, bromo and iodo), and ether such as —OR$^{50}$ wherein R$^{50}$ is hydrocarbyl or substituted hydrocarbyl. In cases in which the functional group may be near a transition metal (Fe) atom, the functional group alone should not coordinate to the metal atom (Fe) more strongly than the groups in those compounds that are shown as coordinating to the metal atom, that is they should not displace the desired coordinating group.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By a "linear α-olefin product" is meant a composition predominantly comprising a compound (or mixture of compounds) of the formula H(CH$_2$CH$_2$)$_q$CH=CH$_2$ wherein q is an integer of 1 to about 18. In most cases, the linear α-olefin product of the present process will be a mixture of compounds having differing values of q of from 1 to 18, with a minor amount of compounds having q values of more than 18. Preferably less than 50 weight percent, and more preferably less than 20 weight percent, of the product will have q values over 18. The product may further contain small amounts (preferably less than 30 weight percent, more preferably less than 10 weight percent, and especially preferably less than 2 weight percent) of other types of compounds such as alkanes, branched alkenes, dienes and/or internal olefins.

By a "primary carbon group" herein is meant a group of the formula —CH$_2$—, wherein the free valence — is to any other atom, and the bond represented by the solid line is to a ring atom of a substituted aryl to which the primary carbon group is attached. Thus the free valence — may be bonded to a hydrogen atom, a halogen atom, a carbon atom, an oxygen atom, a sulfur atom, etc. In other words, the free valence — may be to hydrogen, hydrocarbyl, substituted hydrocarbyl or a functional group. Examples of primary carbon groups include —CH$_3$, —CH$_2$CH(CH$_3$)$_2$, —CH$_2$Cl, —CH$_2$C$_6$H$_5$, —OCH$_3$ and —CH$_2$OCH$_3$.

By a "secondary carbon group" is meant the group

wherein the bond represented by the solid line is to a ring atom of a substituted aryl to which the secondary carbon group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —CH(CH$_3$)$_2$, —CHCl$_2$, —CH(C$_6$H$_5$)$_2$, cyclohexyl, —CH(CH$_3$)OCH$_3$, and —CH=CCH$_3$.

By a "tertiary carbon group" is meant a group of the formula

wherein the bond represented by the solid line is to a ring atom of a substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tetiary carbon groups include —C(CH$_3$)$_3$, —C(C$_6$H$_5$)$_3$, —CCl$_3$, —CF$_3$, —C(CH$_3$)$_2$OCH$_3$, —C≡CH, —C(CH$_3$)$_2$CH=CH$_2$, aryl and substituted aryl such as phenyl and 1-adamantyl.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By a "first ring atom in R$^6$ and R$^7$ bound to an imino nitrogen atom" is meant the ring atom in these groups bound to an imino nitrogen shown in (I), for example

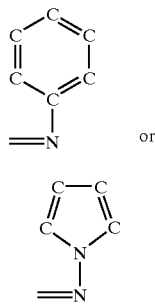

the atoms shown in the 1-position in the rings in (II) and (III) are the first ring atoms bound to an imino carbon atom (other groups which may be substituted on the aryl groups are not shown). Ring atoms adjacent to the first ring atoms are shown, for example, in (IV) and (V), where the open valencies to these adjacent atoms are shown by dashed lines (the 2,6-positions in (IV) and the 2,5-positions in (V)).

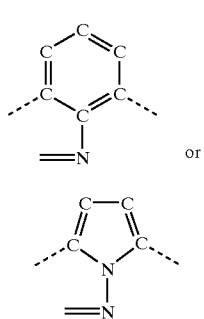

In one preferred compound (I) $R^6$ is

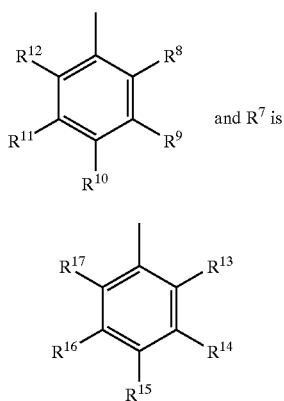

and $R^7$ is wherein:
$R^8$ is a halogen, a primary carbon group, a secondary carbon group or a tertiary carbon group; and
$R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; provided that:
when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or
when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or
when $R^8$ is a tertiary carbon group, none or one of $R^{12}$, $R^{13}$ and $R^{17}$ is tertiary carbon group, with the remainder of $R^{12}$, $R^{13}$, and $R^{17}$ being hydrogen; and
further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

In the above formulas (VI) and (VII), $R^8$ corresponds to the second ring atom adjacent to the first ring atom bound to the imino nitrogen, and $R^{12}$, $R^{13}$ and $R^{17}$ correspond to the other ring atoms adjacent to the first ring atom.

In compounds (I) containing (VI) and (VII), it is particularly preferred that:

if $R^8$ is a primary carbon group, $R^{13}$ is a primary carbon group, and $R^{12}$ and $R^{17}$ are hydrogen; or if $R^8$ is a secondary carbon group, $R^{13}$ is a primary carbon group or a secondary carbon group, more preferably a secondary carbon group, and $R^{12}$ and $R^{17}$ are hydrogen; or if $R^8$ is a tertiary carbon group (more preferably a trihalo tertiary carbon group such as a trihalomethyl), $R^{13}$ is a tertiary carbon group (more preferably a trihalotertiary group such as a trihalomethyl), and $R^{12}$ and $R^{17}$ are hydrogen; or if $R^8$ is a halogen, $R^{13}$ is a halogen, and $R^{12}$ and $R^{17}$ are hydrogen.

In all specific preferred compounds (I) in which (VI) and (VII) appear, it is preferred that $R^1$, $R^2$ and $R^3$ are hydrogen; and/or $R^4$ and $R^5$ are methyl. It is further preferred that:

$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group, more preferably methyl; or $R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group, more preferably ethyl; or $R^9$, $R^{10}$, $R^{11}$, $R^{12}$, $R^{14}$, $R^{15}$, $R^{16}$ and $R^{17}$ are all hydrogen; $R^{13}$ is isopropyl; and $R^8$ is a primary carbon group, more preferably isopropyl; or $R^9$, $R^{10}$, $R^{11}$, $R^{12}$, $R^{13}$, $R^{15}$, $R^{16}$ and $R^{17}$ are all hydrogen; $R^{13}$ propyl; and $R^8$ is a primary carbon group, more preferably n-propyl; or $R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen, more preferably chloro; or $R^9$, $R^{10}$, $R^{11}$, $R^{12}$, $R^{14}$, $R^{15}$, $R^{16}$ and $R^{17}$ are all hydrogen; $R^{13}$ is trihalomethyl, more preferably trifluoromethyl; and $R^8$ is a trihalomethyl, more preferably trifluoromethyl.

In another preferred embodiment of (I), $R^6$ and $R^7$ are, respectively

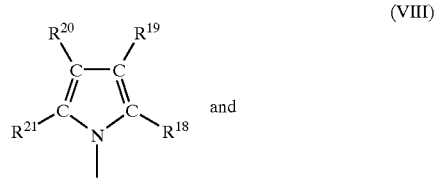

and

-continued

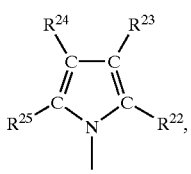
(IX)

wherein
$R^{18}$ is a halogen, a primary carbon group, a secondary carbon group or a tertiary carbon group; and
$R^{19}$, $R^{20}$, $R^{23}$ and $R^{24}$ are each independently hydrogen, hydrocarbyl, substituted hydrocarbyl or a functional group;
Provided that:
when $R^{18}$ is a halogen or primary carbon group none, one or two of $R^{21}$, $R^{22}$ and $R^{25}$ are a halogen or a primary carbon group, with the remainder of $R^{21}$, $R^{22}$ and $R^{25}$ being hydrogen; or
when $R^{18}$ is a secondary carbon group, none or one of $R^{21}$, $R^{22}$ and $R^{25}$ is a halogen, a primary carbon group or a secondary carbon group, with the remainder of $R^{21}$, $R^{22}$ and $R^{25}$ being hydrogen;
when $R^{18}$ is a tertiary carbon group, none or one of $R^{21}$, $R^{22}$ and $R^{25}$ is a tertiary carbon group, with the remainder of of $R^{21}$, $R^{22}$ and $R^{25}$ being hydrogen;
and further provided that any two of $R^{18}$, $R^{19}$, $R^{20}$, $R^{21}$, $R^{22}$, $R^{23}$, $R^{24}$ and $R^{25}$ vicinal to one another, taken together may form a ring.

In the above formulas (VIII) and (IX), $R^{18}$ corresponds to the second ring atom adjacent to the first ring atom bound to the imino nitrogen, and $R^{21}$, $R^{22}$ and $R^{25}$ correspond to the other ring atoms adjacent to the first ring atom.

In compounds (I) containing (VIII) and (IX), it is particularly preferred that:
if $R^{18}$ is a primary carbon group, $R^{22}$ is a primary carbon group, and $R^{21}$ and $R^{25}$ are hydrogen; or
if $R^{18}$ is a secondary carbon group, $R^{22}$ is a primary carbon group or a secondary carbon group, more preferably a secondary carbon group, and $R^{21}$ and $R^{25}$ are hydrogen; or
if $R^{18}$ is a tertiary carbon group (more preferably a trihalo tertiary carbon group such as a trihalomethyl), $R^{22}$ is a tertiary carbon group (more preferably a trihalotertiary group such as a trihalomethyl), and $R^{21}$ and $R^{25}$ are hydrogen; or
if $R^{18}$ is a halogen, $R^{22}$ is a halogen, and $R^{21}$ and $R^{25}$ are hydrogen.

In all specific preferred compounds (I) in which (VIII) and (IX) appear, it is preferred that $R^1$, $R^2$ and $R^3$ are hydrogen; and/or $R^4$ and $R^5$ are methyl. It is further preferred that:
$R^{19}$, $R^{20}$, $R^{21}$, $R^{23}$ and $R^{24}$ are all hydrogen; $R^{22}$ is methyl; and $R^{18}$ is a primary carbon group, more preferably methyl; or
$R^{19}$, $R^{20}$, $R^{21}$, $R^{23}$ and $R^{24}$ are all hydrogen; $R^{22}$ is ethyl; and $R^{18}$ is a primary carbon group, more preferably ethyl; or
$R^{19}$, $R^{20}$, $R^{21}$, $R^{23}$ and $R^{24}$ are all hydrogen; $R^{22}$ is isopropyl; and $R^{18}$ is a primary carbon group, more preferably isopropyl; or
$R^{19}$, $R^{20}$, $R^{21}$, $R^{23}$ and $R^{24}$ are all hydrogen; $R^{22}$ is n-propyl; and $R^{18}$ is a primary carbon group, more preferably n-propyl; or
$R^{19}$, $R^{20}$, $R^{21}$, $R^{23}$ and $R^{24}$ are all hydrogen; $R^{22}$ is chloro or bromo; and $R^{18}$ is a halogen, more preferably chloro or bromo.

Compound (I) and its iron complexes (the oligomerization catalyst) may be prepared by a variety of methods, see for instance previously incorporated U.S. Pat. No. 5,955,555 and U.S. Pat. No. 6,103,946, as well as U.S. Pat. No. 6,232,259 and WO00/08034, both of which are also incorporated by reference herein for all purposes as if fully set forth.

It is preferred herein to react an iron complex of (I), such as a complex of (I) with $FeCl_2$, with the cocatalyst (e.g., the alkylaluminum compound), preferably an aluminoxane such as methylaluminoxane, to form an active ethylene oligomerization species. The molar ratio of aluminum (as alkylaluminum compound) to iron (as a complex) in the oligomerization preferably is about 2000 or less. A more preferred upper limit is about 1500 or less, still more preferably about 1000 or less, and especially about 700 or less; and as a lower limit is about 5 or more, more preferably about 10 or more, still more preferably about 100 or more, even more preferably about 300 or more, and especially about 500 or more. For clarity, any combination of the aforementioned upper and lower limits may be used to define a preferred range herein such as, for example, from about 5 to about 1500, from about 5 to about 1000, from about 100 to about 1000, from about 500 to about 700, and other other such combination.

Another preferred range in accordance with the present invention is from about 5 to about 300. Within this range, a more preferred lower limit is about 10 or more, more preferably about 20 or more, still more preferably about 30 or more, and especially about 50 or more; and a more preferred upper limit about 200 or less, still more preferably about 150 or less, and especially about 100 or less. Again for clarity, any combination of the aforementioned upper and lower limits may be used to define a preferred range herein.

It should be noted that the above ranges refer to steady state operating conditions. Under certain circumstances, it may be beneficial to start the reaction under higher Al:Fe ratios then, in the course of the process stabilizing, lower the Al:Fe ratio to the desired steady state level. For example, the reaction could be started at above any of the upper ratio limits mentioned above, then reduced to the desired level at or above any of the lower ratio limits mentioned above.

Preferred alkylaluminum compounds include one or more of $R^{51}{}_3Al$, $R^{51}AlCl_2$, $R^{51}{}_2AlCl$, and "$R^{51}AlO$" (alkylaluminoxanes), wherein $R^{51}$ is alkyl containing 1 to 25 carbon atoms, preferably 1 to 4 carbon atoms. Specific alkylaluminum compounds include methylaluminoxane (which is an oligomer with the general formula $(MeAlO)_n$), $(C_2H_5)_2AlCl$, $C_2H_5AlCl_2$, $(C_2H_5)_3Al$ and $((CH_3)_2CHCH_2)_3Al$. A preferred alkylaluminum compound is an aluminoxane, especially methyl aluminoxane.

The conditions for the oligomerization described in previously incorporated U.S. Pat. No. 6,103,946 and parent application Ser. No. 09/906,974 (filed Jul. 17, 2001), entitled "MANUFACTURING PROCESS FOR ALPHA-OLEFINS", may otherwise be followed.

For example, the oligomerization reaction may be run at a wide range of temperatures generally ranging from about −100° C to about +300° C., preferably about 0° C. to about 200° C., and more preferably about 20° C. to about 100° C. Pressures may also vary widely, ranging from an ethylene pressure (gauge) of from about 0 kPa to about 35 MPa, more preferably from about 500 kPa to about 15 MPa.

The process may be run in gas or liquid phase, but is typically run in liquid phase, preferably using an aprotic organic liquid. The process ingredients and products may or may not be soluble in these liquids, but obviously these liquids should not prevent the oligomerization from ocurring. Suitable liquids include alkanes, alkenes, cycloalkanes, selected halogenated hydrocarbons and aromatic hydrocarbons. Specific useful liquids include hexane, toluene, benzene and the α-olefins themselves.

The ethylene oligomerizations herein may also initially be carried out in the solid state by, for instance, supporting and active catalyst and/or aluminum compound on a substrate such as silica or alumina. Alternatively a solution of the catalyst precursor may be exposed to a support having an alkylaluminum compound on its surface. These "heterogeneous" catalysts may be used to catalyze oligomerization in the gas phase or the liquid phase. By "gas phase" is meant that the ethylene is transported to contact with the catalyst particle while the ethylene is in the gas phase. In general, the oligomerization may be run as a continuous gas phase, solution or slurry processes.

It is particularly preferred to run the oligomerization as "essentially single phase liquid full", which means that at least 95 volume percent of the reactor volume is occupied by a liquid that is a single phase. Small amounts of the reactor volume may be taken up by gas, for example ethylene may be added to the reactor as a gas, which dissolves rapidly under the process conditions. Nevertheless, some small amount of dissolving ethylene gas may be present. Not counted in the reactor volume is any solid resulting from fouling of the reactor. See, for example, previously incorporated parent application Ser. No. 09/906,974 (filed Jul. 17, 2001), entitled "MANUFACTURING PROCESS FOR ALPHA-OLEFINS".

These molar ratios of Al:Fe described herein are based on the process ingredients, that is, the ingredients comprising the reactor feed; therefore, it is preferred at such low molar Al:Fe ratios to purify the process ingredients so that the alkylaluminum compounds are not "used up" reacting with moisture or other impurities.

Using the oligomerization catalysts described herein a mixture of α-olefins is obtained. A measure of the molecular weights of the olefins obtained is factor K from the Schulz-Flory theory (see for instance B. Elvers, et al., Ed. *Ullmann's Encyclopedia of Industrial Chemistry*, Vol. A13, VCH Verlagsgesellschaft mbH, Weinheim, 1989, p. 243–247 and 275–276). This is defined as:

$$K=n(C_{n+2} \text{ olefin})/n(C_n \text{ olefin})$$

wherein $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting oligomeric reaction product mixture. The K factor is preferred to be in the range of about 0.65 to about 0.8 to make the α-olefins of the most commercial interest. This factor can be varied to some extent, see for instance previously incorporated U.S. Pat. No. 6,103,946 and parent application Ser. No. 09/906,974 (filed Jul. 17, 2001), entitled "MANUFACTURING PROCESS FOR ALPHA-OLEFINS".

What is claimed is:

1. A continuous process for the production of a linear α-olefin product, comprising the step of contacting, in a continuous reactor, process ingredients comprising an ethylene oligomerization catalyst composition, ethylene and a co-catalyst, wherein:

(a) the ethylene oligomerization catalyst composition comprises an iron complex of a compound of the formula

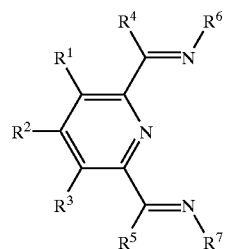

wherein:
$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:
in $R^6$, a second ring atom adjacent to said first ring atom is bound to a halogen, a primary carbon group, a secondary carbon group or a tertiary carbon group; and further provided that
in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or
in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or
in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom;

(b) the cocatalyst comprises an alkyl aluminum compound; and (c) the molar ratio of Al in the cocatalyst to Fe in the ethylene oligomerization catalyst is about 2000 or less.

2. The process of claim 1, wherein said molar ratio is from about 100 to about 1500.

3. The process of claim 1, wherein said molar ratio is from about 300 to about 1000.

4. The process of claim 1, wherein said molar ratio is from about 500 to about 700.

5. The process of claim 1, wherein said molar ratio is from about 5 to about 300.

6. The process of claim 1, wherein the continuous reactor is essentially single phase liquid full.

7. An improved continuous process for the production of a linear α-olefin product, the production process comprising the step of contacting, in a continuous reactor, process ingredients comprising an ethylene oligomerization catalyst composition, ethylene and a cocatalyst, wherein:

(a) the ethylene oligomerization catalyst composition comprises an iron complex of a compound of the formula

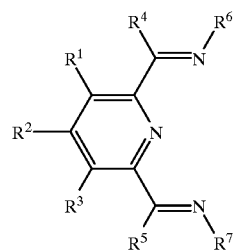 (I)

wherein:
- $R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;
- $R^4$ and $R^5$ are each independently hydrogen, hydrocarbyl, substituted hydrocarbyl or an inert functional group;
- $R^6$ and $R^7$ are each independently a substituted aryl having a first ring atom bound to the imino nitrogen, provided that:
  - in $R^6$, a second ring atom adjacent to said first ring atom is bound to a halogen, a primary carbon group, a secondary carbon group or a tertiary carbon group; and further provided that
  - in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or
  - in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or
  - in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom; and (b) the cocatalyst comprises an alkyl aluminum compound;

wherein the improvement comprises reducing the formation of polyethylene waxes and polymers in the linear α-olefin product by contacting the process ingredients at a molar ratio of Al in the cocatalyst to Fe in the ethylene oligomerization catalyst of about 2000 or less.

8. The process of claim 7, wherein said molar ratio is from about 100 to about 1500.

9. The process of claim 7, wherein said molar ratio is from about 300 to about 1000.

10. The process of claim 7, wherein said molar ratio is from about 500 to about 700.

11. The process of claim 7, wherein said molar ratio is from about 5 to about 300.

12. The process of claim 7, wherein the continuous reactor is essentially single phase liquid full.

* * * * *